(12) United States Patent
Dettinger et al.

(10) Patent No.: US 10,467,383 B2
(45) Date of Patent: Nov. 5, 2019

(54) DERIVED OBSERVATIONS IN CARE PLAN ADMINISTRATION

(71) Applicant: PREVENTICE, INC., Rochester, MN (US)

(72) Inventors: Richard D. Dettinger, Rochester, MN (US); Richard M. Smith, Oronoco, MN (US); James Dean Hutchins, Kernersville, NC (US)

(73) Assignee: Preventice Solutions, Inc., Rochester, MN (US)

( * ) Notice: Subject to any disclaimer, the term of this patent is extended or adjusted under 35 U.S.C. 154(b) by 701 days.

(21) Appl. No.: 14/508,391

(22) Filed: Oct. 7, 2014

(65) Prior Publication Data

US 2016/0098537 A1 Apr. 7, 2016

(51) Int. Cl.
| | |
|---|---|
| *G06F 19/00* | (2018.01) |
| *G16H 40/63* | (2018.01) |
| *A61B 5/00* | (2006.01) |
| *A61B 5/021* | (2006.01) |
| *A61B 5/024* | (2006.01) |
| *A61B 5/0468* | (2006.01) |

(52) U.S. Cl.
CPC ........ *G06F 19/3475* (2013.01); *A61B 5/4833* (2013.01); *G16H 40/63* (2018.01); *A61B 5/021* (2013.01); *A61B 5/024* (2013.01); *A61B 5/0468* (2013.01)

(58) Field of Classification Search
CPC ..... G06C 50/22–50/24; G06F 19/322–19/327; G06Q 50/22–50/24; A61B 5/4833; G16H 10/00
See application file for complete search history.

(56) References Cited

U.S. PATENT DOCUMENTS

| | | | | |
|---|---|---|---|---|
| 6,440,066 | B1 * | 8/2002 | Bardy | A61B 5/0002 128/923 |
| 2003/0191666 | A1 * | 10/2003 | Kline | G06F 17/18 705/2 |
| 2006/0173712 | A1 * | 8/2006 | Joubert | G06F 19/322 705/2 |
| 2011/0238439 | A1 * | 9/2011 | Rice | G06F 19/325 705/2 |
| 2011/0245633 | A1 * | 10/2011 | Goldberg | A61B 5/681 600/301 |

\* cited by examiner

*Primary Examiner* — Sheetal R Paulson
(74) *Attorney, Agent, or Firm* — Patterson + Sheridan, LLP (57) ABSTRACT

Techniques presented herein disclose a method for generating a derived observation for a care plan assigned to a patient. According to one embodiment, an application executing on a care platform server receives an event log having a plurality of events. Each event includes one or more types of biometric data for the patient. The care plan includes one or more definitions for metrics that are derived from the one or more types of biometric data. A temporal slice of the event log is selected based on one or more of the definitions. The derived metrics are generated by evaluating events within the selected temporal slice of the event log against one or more of the definitions. A condition of the patient is evaluated based on the derived metrics.

20 Claims, 6 Drawing Sheets

DERIVED OBSERVATIONS IN CARE PLAN ADMINISTRATION

BACKGROUND

Field

Embodiments of the present disclosure generally relate to a health care, and more specifically, to a health care plan that generates derived observations from data received from a patient.

Description of the Related Art

In the health care field, a care plan is a set of tasks provided by a health care practitioner (e.g., a doctor) to a patient. Historically, such a care plan is a written document that provides directions and routines for the patient to follow to manage certain health conditions. The care plan may include a set of tasks (e.g., exercise for a given duration) for the patient to perform, content that educates the patient about a diagnosed condition (e.g., brochures describing the diagnosed condition), and logs for the patient to periodically record information in (e.g., weight, blood pressure, etc.). As an example, a doctor might create a care plan for a patient with hypertension that includes several brochures describing hypertension and hypertension treatment and assigned tasks such as walking on a treadmill for thirty minutes each morning, drinking a glass of water every three hours, and recording blood pressure at the end of each day. Thus, as part of the treatment of the condition, the patient is expected to adhere to the tasks listed in the care plan and to then follow up with the doctor in a subsequent appointment to assess the patient's progress.

The current care plan approach has several shortcomings. For instance, a care plan for a particular condition is often tailored towards the condition itself, without considering relevant details about a patient. Typically, once a doctor has diagnosed a patient with a particular condition, the doctor prints out a "one size fits all" care plan for the individual that instructs the individual on how to manage the condition. Under such a care plan, the doctor often has no way of determining the patient's adherence to the care plan until a follow-up appointment. Further, a paper care plan may be limited in types of data that can be collected from a patient. As a result, a doctor might not have as much information needed to make a meaningful analysis. For example, a care plan may require the patient to record his heart rate at different points of the day. Although the doctor may use the patient's pulse readings in analyzing the patient's condition for a given day, the doctor may want other patient metrics to provide a fuller analysis.

SUMMARY

One embodiment presented herein describes a method for generating a derived observation for a care plan assigned to a patient. The method generally includes receiving, via a processor, an event log having a plurality of events. Each event includes one or more types of biometric data for the patient. The care plan includes one or more definitions for metrics that are derived from the one or more types of biometric data. The method also includes selecting a temporal slice of the event log based on one or more of the definitions. Derived metrics are generated by evaluating events within the selected temporal slice of the event log against one or more of the definitions. A condition of the patient is evaluated based on the derived metrics.

Still another embodiment includes a computer-readable storage medium storing instructions, which, when executed on a processor, perform an operation for generating a derived observation for a care plan assigned to a patient. The operation itself includes receiving, via a processor, an event log having a plurality of events. Each event includes one or more types of biometric data for the patient. The care plan includes one or more definitions for metrics that are derived from the one or more types of biometric data. The operation also includes selecting a temporal slice of the event log based on one or more of the definitions. Derived metrics are generated by evaluating events within the selected temporal slice of the event log against one or more of the definitions. A condition of the patient is evaluated based on the derived metrics.

Still another embodiment includes a system having a processor and a memory a memory storing one or more application programs configured to perform an operation for generating a derived observation for a care plan assigned to a patient. The operation itself includes receiving, via a processor, an event log having a plurality of events. Each event includes one or more types of biometric data for the patient. The care plan includes one or more definitions for metrics that are derived from the one or more types of biometric data. The operation also includes selecting a temporal slice of the event log based on one or more of the definitions. Derived metrics are generated by evaluating events within the selected temporal slice of the event log against one or more of the definitions. A condition of the patient is evaluated based on the derived metrics.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, may admit to other equally effective embodiments.

To facilitate understanding, identical reference numerals have been used, where possible, to designate identical elements that are common to the figures. It is contemplated that elements and features of one embodiment may be beneficially incorporated in other embodiments without further recitation.

DETAILED DESCRIPTION

Current approaches for providing a care plan to a patient are rigid. For example, in many cases, a physician who has diagnosed a particular condition in a patient may provide the patient with a generalized care plan commonly used to address that condition. Frequently, these generalized care plans are pre-printed documents that are not tailored to any particular patient but rather generally address the diagnosed medical condition. However, although the care plans may provide information that allows the doctor to analyze the patient's condition as the patient progresses through the care plan, the information may, at times, be insufficient for the doctor to provide a more meaningful analysis. For example, the doctor may be interested in the patient's average heart rate over the course of a day, which might be impractical to obtain through the current approach.

Embodiments presented herein describe techniques for generating derived observations from data observed from a patient for a care plan assigned to the patient. In one embodiment, a care platform allows a physician to design a care plan tailored specifically for an individual patient. The care plan may include multiple care plan protocols, with each of the care plan protocols addressing a respective medical condition the patient has been diagnosed with. Generally, a care plan protocol describes the treatment of a particular medical condition. For instance, a care plan could specify a set of specific tasks that a patient follows to manage a particular condition and could divide the tasks by phases and schedules. The care plan protocol may divide the tasks by phases and schedules. Further, a care plan protocol may be available for a variety of conditions, such as congestive heart failure, diabetes, sprained ankle, etc.

In addition, the care protocol may specify metrics that the care platform monitors during the patient's treatment, thresholds to detect for each metric, and remedial actions to be taken in response to detecting such thresholds. One example metric is blood pressure. The blood pressure metric may be associated with thresholds indicating values and conditions in which the care platform performs some action in response to detecting such values and conditions, e.g., sending instructions to the patient to rest for a given period of time. Further, the care protocol may provide the patient with resources to educate the patient about a diagnosed condition, treatment, and the like (e.g., instructional videos, articles, etc.). The care platform provides a template for each care plan protocol. The care platform may consolidate the configured care plan protocols into one overall care plan for the patient.

Once created, the care platform may transmit the care plan to an application in a device owned by the patient, e.g., a smart phone or tablet device. Though the device, the patient may access the care plan and understand the tasks to perform. Further, the application may receive information from various sensors that monitor patient activity (e.g., heart rate, weight, blood pressure). In addition, the mobile application may prompt the patient to report symptoms experienced. The application can record the information to the care plan and relay information to the care platform, which stores the information to an event log and also makes the information available to the physician (e.g., via a portal interface). Doing so allows the physician to monitor the patient's adherence to the care plan.

Likewise, the care platform may monitor the patient's adherence to the care plan based on sensor data and reported symptoms received (e.g., from the mobile application). Further, in one embodiment, the care platform may generate derived observations based on the received metrics. The derived observations may be used in various ways, e.g., by a doctor in analyzing the patient's condition, by the care platform in generating subsequently derived observations, etc. A derived observation is a predefined metric that is calculated using metrics obtained from the various sensors, e.g., raw metrics obtained from the sensor devices. In addition, the derived observations can be generated from non-sensor data, such as other derived observations, classification records, etc.

For instance, assume that a sensor device can capture premature ventricular contractions (PVCs) of the patient. Because PVCs commonly occur in many individuals, a single observation of a PVC might not provide meaningful information but may instead be more useful when collected over time. For example, a doctor may want to compare an average count of PVCs detected during daytime with an average count detected during nighttime. Therefore, the care platform may generate a derived observation based on event data (e.g., raw biometric data, timestamps, etc.) for the average PVC count per hour over a given period.

The care platform maintains a repository of derived observation definitions. In one embodiment, to generate a derived observation, the care platform receives incoming data from the patient. As stated, the care platform records the data in an event log. In one embodiment, the event log comprises one or more database tables within a database. For instance, whenever the sensor devices capture events, the care platform could insert each event as a record in a database table. The record may include an event description, event type, timestamp information, an indexing number, and the like. In one embodiment, the care platform is configured to insert the records into the database table at a position determined based on a relatively priority of the event in question. As an example, the care platform could insert an event having a higher relative priority at a position closer to the front of the event log, so that the event will be processed more quickly.

As the care platform receives event data, the care platform determines whether any of the event data may be used in a derived observation definition. If so, the care platform identifies a subset of the events in the event log that satisfies the derived observation definition. If the subset of events completely satisfies the derived observation definition, then the care platform generates the derived observation based on the definition. Note, the care platform may evaluate derived observations from definitions that are relevant to a care plan for a given patient. For example, assume the care platform has definitions for a derived observation that measures weight loss over a given period and another derived observation that measures PVC observations over a given period. In such a case, a care plan targeting only diabetes might evaluate the derived observation for weight loss over the period and not evaluate PVC observations.

Continuing the previous example, a derived observation definition for an average amount of PVCs detected over a 12-hour interval may specify a time window (e.g., starting at 8:00 AM and ending at 8:00 PM), types of data to obtain (e.g., PVC observations, timestamps for the PVC observations, etc.), and the like. For instance, the care platform could evaluate temporal slices of events periodically (e.g., once every fifteen minutes, once every hour, etc.) using a derived observation definition to calculate a derived observation value, and could determine whether the calculated derived observation value satisfies any conditional thresholds specified within the care plan. The intervals may be configured in the care plan, as well. When the care platform receives data that satisfies the definition, the care platform calculates the derived observation using the metrics specified in the definition. The care platform may then record the derived observation in the care plan for later use. For example, the care plan may specify to notify a care provider if the derived observation is over a given threshold. As another example, if the derived observation is over a given threshold, the care platform may initiate a treatment process (e.g., by inserting additional tasks to the care plan) aimed at orienting the derived observation (and other associated metrics) to a desired level. As the care platform subsequently observes metrics and derived observations, the care platform can continually adjust the treatment process.

Figure 1A:
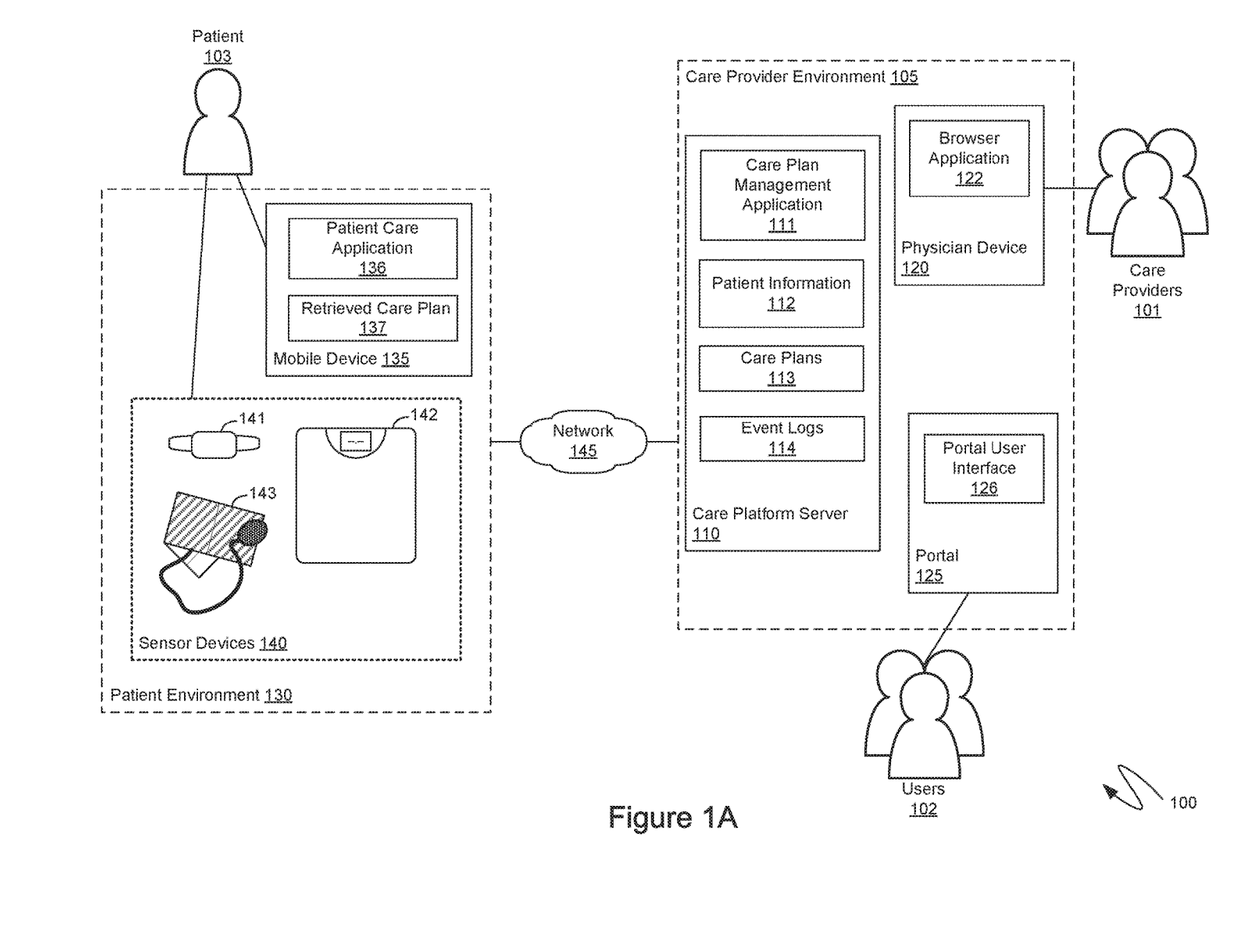
FIG. 1A illustrates an example computing environment, according to one embodiment.

FIG. 1A illustrates an example computing environment 100, according to one embodiment. As shown, the computing environment 100 may include a care provider environment 105 and a patient environment 130, each connected to one another via a network 145. The environments 105 and 130 allow a patient 103 to communicate with a care provider 101 (e.g., a physician).

The care provider environment 105 includes a care platform server 110, a physician device 120, and a portal 125. Each of the care platform server 110, physician device 120, and portal 125 may be a physical computing system or may be a virtual computer instance (e.g., executing in a cloud computing platform). A care provider 101 may use the physician device 120 to access (e.g., via a browser application 122) a portal user interface 126 hosted by the portal 125. The portal user interface 126 itself provides users 102 (e.g., the care providers 101) with access to the care platform server 110.

The care platform server 110 includes various applications and data that allow a care provider 101 to manage a care plan for a patient 103. As shown, the care platform server 110 includes a care plan management application 111, patient information 112, care plans 113, and event logs 114.

A care plan 113 may include one or more care protocols with each of the care protocols relating to a respective medical condition the patient has been diagnosed with. Generally, each care protocol could specify a set of tasks that a patient 103 follows to manage a certain condition, metrics that the care plan management application 111 monitors, derived observations based on those metrics, objectives for the patient, and the like. For instance, a care protocol may target recovery from a heart attack. Another care protocol may treat diabetes. Tasks associated with a care protocol may include steps such as exercising for a specified duration or taking medication at a certain time of day. Other tasks may prompt the user to report current symptoms to the care platform server 110. Further, each care plan protocol may be divided into different phases. The phases may represent different stages of care for a particular condition, e.g., a recovery phase, a maintenance phase, etc.

For example, a care protocol for weight management may include several phases. A patient 103 may begin the care protocol at a weight loss phase, where tasks may include performing strenuous exercises frequently, and where thresholds may specify further actions that the care plan management application 111 takes if the patient 103 loses X amount of weight or gains Y amount of weight. For example, if the metrics indicate that the patient 103 gained Y amount of weight after a period at which the patient 103 had a Z average activity level, the care plan management application 111 may instruct the patient 103 to watch an educational video in response. Continuing the example, if the patient 103 loses X amount of weight during a given period, the care plan management application 111 may transition the care protocol to a weight maintenance phase, where tasks may include exercises that assist the patient 103 in maintaining the weight.

Each care plan protocol may also include thresholds associated with monitored metrics (and observations derived from those metrics) and could further specify an action(s) to be taken responsive to an observation threshold being satisfied. The care platform server 110 may monitor the adherence of a patient 103 through various sensor devices 140 that can measure heart rate, weight, blood pressure, and the like. The care platform server 110 may take action if one of the metrics exceeds a corresponding threshold, e.g., if a patient 103 gains 1.5 pounds after a day, the platform server 110 may modify the care plan 113.

The care plan management application 111 generates a care plan 113 for a patient 103 based on care plan protocols selected and customized by the care provider 101. The care plan management application 111 may store the care plan 113 on the care platform server 110. Further, the care plan management application 111 transmits the care plan 113 to a mobile device 135 (e.g., to a patient care application 136 executing on the mobile device 135) of the patient 103. The patient 103 views the care plan (shown as retrieved care plan 137) on the mobile device through the patient care application 136. Doing so allows the patient 103 to understand tasks needed to adhere to the platform.

Moreover, the mobile device 135, upon receiving the care plan, could configure one or more sensor devices 140 to monitor one or more patient metrics as specified by the care plan. For example, the mobile device 135 could configure logic on a heart rate monitor device worn by the patient to monitor the patient's heart rate and to detect when the patient's heart rate exceeds a threshold number of beats per minute specified within the care plan. The heart rate monitor device, upon detecting that the threshold condition has been satisfied, could transmit an alert to the mobile device 135, which could in turn perform an action as specified by the care plan. For example, the mobile device 135, upon receiving the alert, could display a notification to the patient, informing the patient that his heart rate is elevated and instructing the patient to sit down and rest for a period of time. As another example, the mobile device 135 could generate a notification to the care plan management application 111, informing the care plan management application 111 that the patient's heart rate exceeds the threshold amount of beats per minute.

The patient care application 136 may display information related to the retrieved care plan 137, such as phases, tasks, and other information about conditions targeted for treatment by the retrieved care plan 137. When the patient 103 performs a task, the patient 103 records progress in the patient care application 136. The patient care application 136 relays this information to the care plan management application 111. Doing so allows the care provider 101 to monitor the biometrics of the patient 103 and adherence to the care plan.

As stated, sensor devices 140 may send biometric information to the patient care application 136. As shown, such sensor devices 140 may include an adhesive body sensor 141, a weighing scale 142, and a blood pressure cuff 143. More generally, any device capable of collecting data associated with a patient may be used, consistent with the present disclosure. Each of the sensor devices 140 may capture different biometrics of the patient 103. For example, when applied to the body of patient 103, the adhesive body sensor 141 captures biometric data (e.g., heart rate) in real-time. In addition, each of the sensor devices 140 may be configured to transmit the biometrics electronically to the patient care application 136. In turn, the patient care application 136 sends the captured biometrics to the care plan management application 111.

In one embodiment, the care plan management application 111 may generate derived observations from the captured biometric information. Derived observations are generally metrics that are calculated from other metrics observed by the care plan management application 111, such as raw metrics obtained from the sensor devices 140 or other derived observations. Examples of derived observations include biometric trends, such as weight gain or loss over a period of time, an average count of PVC observations over time, change in blood glucose level over a period of time, QT intervals for a patient's heart rate, etc. Another example includes weight gain relative to the patient's caloric intake. Such a derived observation may be useful to a care provider in the event that a patient gains weight despite having a controller caloric intake. The care provider may be able to determine causes related to the weight gain, such as recently prescribed medications, latent conditions, etc.

In one embodiment, the care platform server 110 includes one or more derived observation definitions. Each definition specifies criteria for data, data types, and conditions for generating a particular derived observation. For instance, a derived observation for a QT interval may include criteria specifying heart rate readings and timestamps associated with each reading. In one embodiment, the derived observation definitions are created in accordance with patient information 112 and policies of the care provider 101. Patient information 112 may include treatment history of the patient 103.

The care plan management application 111 stores data and metrics obtained from sensors and generated as derived observations into an event log 114. Each event may in the log 114 may be classified based on a type of data received, priority, etc. In one embodiment, the sensor devices 140, upon detecting an observation threshold has been reached, are configured to perform an initial classification of the event. In a particular embodiment, the mobile device 135 is configured to perform the initial classification of the event. For example, the body sensor 141, upon detecting that the ECG data collected from the patient 103 indicates an erratic heart behavior, could classify the event as a cardiac event. This initial classification, along with the relevant ECG data (e.g., ECG data a predetermined length of time before and after the event), could be transmitted to the mobile device 135 (e.g., over a Bluetooth® communications link) and the patient care application 136 could then forward the event data on to the care plan management application 111 over the network 145 (e.g., the Internet). Upon receiving the event data, the care plan management application 111 could detect that the event was initially classified as a cardiac event and could perform a more detailed analysis of the event data to more accurately classify the event. For example, the care plan management application 111 could be configured recognize a number of sub-classifications of cardiac events and could analyze the received event to determine which of the sub-classifications best matches the event data. The care plan management application 111 could then record the determined sub-classification. In some situations, the care plan 113 for the patient 103 could specify a particular treatment plan to perform upon determining a particular sub-classification of event. In such a situation, the care plan management application 111 could transmit a request to the patient care application 136 to initiate the treatment plan on the mobile device 135. Doing so allows for a more computationally expensive analysis of the event data to be performed using the computing resources of the care provider environment 105, rather than the limited resources of the sensor devices 140 or the mobile device 135, while quickly determining an initial classification for the event using the sensor devices 140.

Figure 1B:
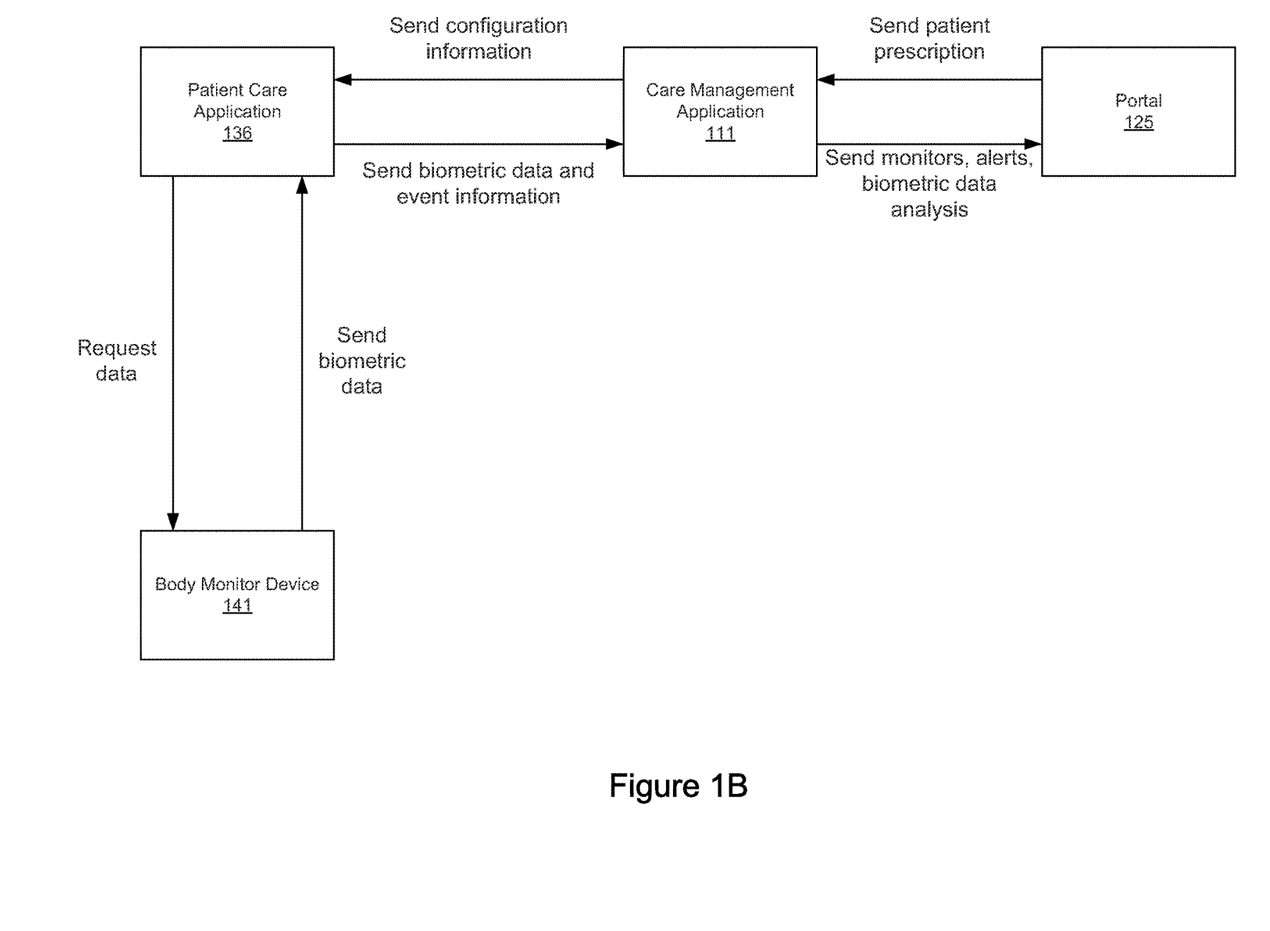
FIG. 1B illustrates an example usage of the care platform architecture, according to one embodiment.

FIG. 1B illustrates an example usage of the care platform architecture, according to one embodiment. More specifically, FIG. 1B illustrates the interactions between each component of the care platform. A care provider 101 may submit a patient's prescription information as well as care plan configuration to the portal 125. The portal 125 relays this information to the care plan management application 111. The care plan management application 111 generates the care plan and sends configuration information related to the care plan to the patient care application 136. Once the patient care application 136 is configured with the care plan, the patient care application 136 can request the body monitor device 141 to send data. As stated, the body monitor device 141 obtains biometric readings, such as ECG readings, heart rate readings, and the like from the patient 103. The body monitor device 141 sends biometric data to the patient care application 136.

Illustratively, the patient care application 136 relays biometric data and event information to the care plan management application 111 as received from the body monitor device 141. The care plan management application 111 processes the biometric data, e.g., by evaluating the data to determine whether the biometrics exceed certain thresholds, by generating derived observations, recording the biometrics to the care plan, etc. Further, the care plan management application 111 may send alerts and analysis for the biometric data to the portal 125 for the care provider 101 to view.

Figure 2:
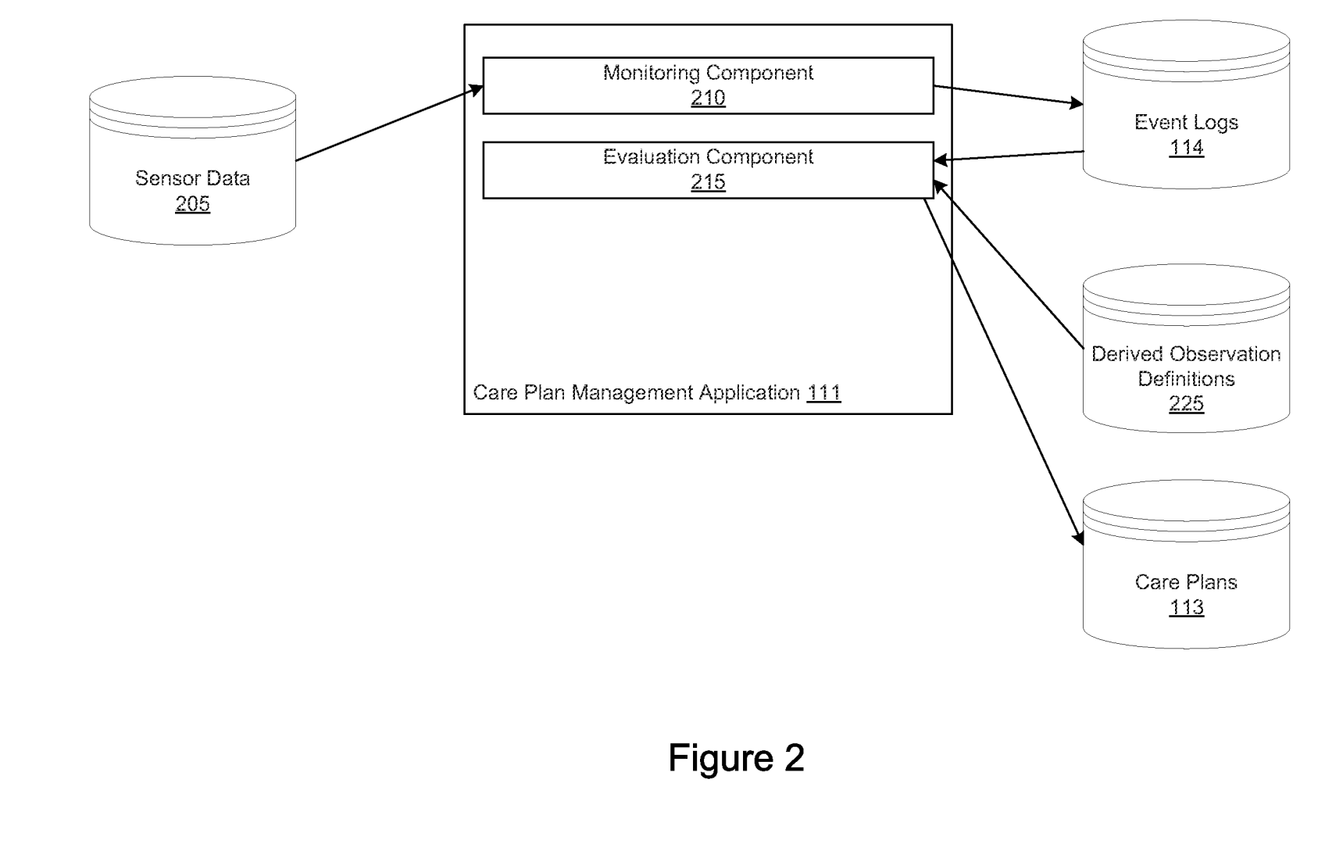
FIG. 2 further illustrates the care plan management application described in FIGS. 1A and 1B, according to one embodiment.

FIG. 2 further illustrates the care plan management application 111, according to one embodiment. As stated, the care plan management application 111 modifies a care plan 113 based on sensor data 205 retrieved from a patient 103. As shown, the care plan management application 111 further includes a monitoring component 210 and an evaluation component 215.

The monitoring component 210 receives sensor data 205, i.e., biometric information of a patient 103, from the patient care application 136. The monitoring component 210 stores the sensor data 205 in an event log 114 associated with the care plan 113 assigned to the patient 103. Each event may group data based on a time at which the data was gathered, data types, etc.

The evaluation component 215 identifies event data that satisfies one or more derived observation definitions 225 and generates derived observations based on the definitions 225. As the monitoring component 210 records biometric information to the event log 114, the evaluation component 215 determines whether any of the information provided satisfies one of the derived observation definitions 225. Each derived observation definition 225 may provide various criteria to be satisfied, such as certain biometric types, time ranges, numeric value ranges, etc. If the criteria is satisfied, then the evaluation component 215 generates the derived observation based on the definition 225 and records the definition to the care plan 113.

For example, assume that a care plan 113 assigned to a patient 103 is targeted towards recovery from congestive heart failure. Also assume the care plan 113 tracks PVC trends occurring in the patient 103, such as an average amount of PVCs per hour for a given time span. Such trends may be expressed as derived observations from PVC metrics observed from the patient 103 over time. A care provider 101 may create a derived observation definition 225 that the evaluation component 215 uses to generate such observations. The derived observation definition may include bounds (e.g., time ranges, numeric ranges, etc.) and types of values needed to generate the observation. In one embodiment, the care plan management application 111 may evaluate temporal slices of the event log 114 at specified intervals (e.g., every hour, every thirty minutes, etc.). The care plan management application 111 identifies events in the slice that satisfy criteria in the definition.

Once generated, the evaluation component 215 may record the observation in the care plan 113. Doing so allows the care provider 101 to track the derived observation (e.g., through the portal) and make further analyses of the patient's condition. Further, the care plan management application 111 may be treated as another type of metric for use in observation thresholds, tasks, and other aspects of the care plan 113. Likewise, derived observation definitions 225 may specify other derived observations as metrics used to generate other derived observations. For example, a derived observation definition 225 can specify a derived observation that includes an aggregate of average PVC count per 12-hour duration derived observations over a week period.

Figure 3:
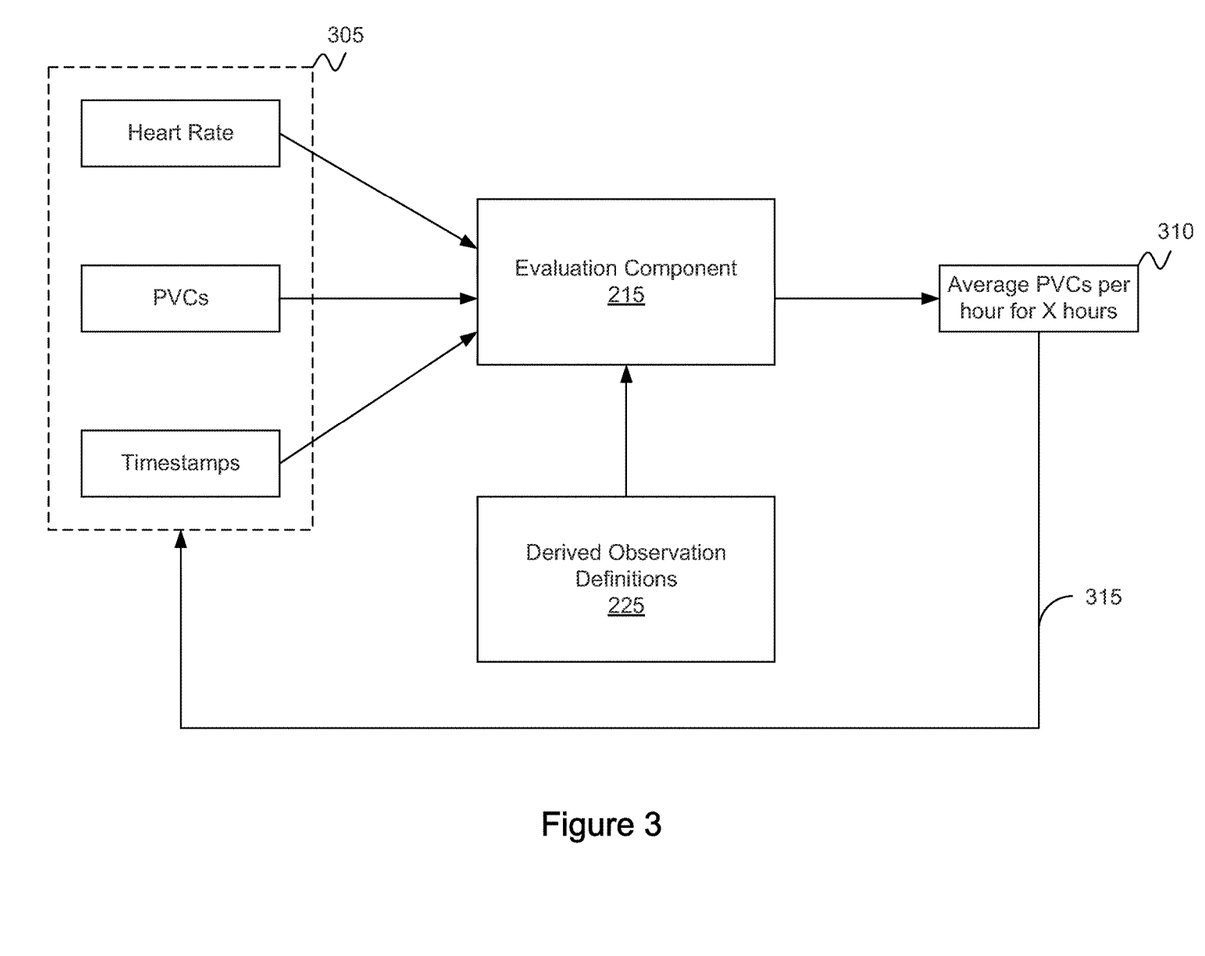
FIG. 3 illustrates an example of the evaluation component described in FIG. 2 generating a derived observation, according to one embodiment.

FIG. 3 illustrates an example of the evaluation component 215 generating a derived observation for an average count of PVCs per hour for a given duration (e.g., every twelve hours), according to one embodiment. Assume that one of the derived observation definitions 225 includes a definition for the average count of PVCs per hour for the duration. Further, assume that the criteria for the derived observation require heart rates and PVCs to be collected from the patient over a twelve-hour span. Illustratively, event data 305 including heart rate metrics, PVC metrics, and timestamps are input to the evaluation component 215. The event data 305 correspond to metrics observed from a patient via sensor devices 140.

The evaluation component 215 determines whether the values, types, and timestamps included in the event data 205 satisfies criteria specified in any of the derived observation definitions 225. Continuing the previous example, assume that the event data 305 satisfies the criteria for the derived observation. In response, the evaluation component 215 generates the average PVCs per hour for the duration, as shown by the derived observation 310. Once generated, the derived observation 310 may be used as an additional metric used to generate other derived observations (as illustrated by the arrow 315).

Figure 4:
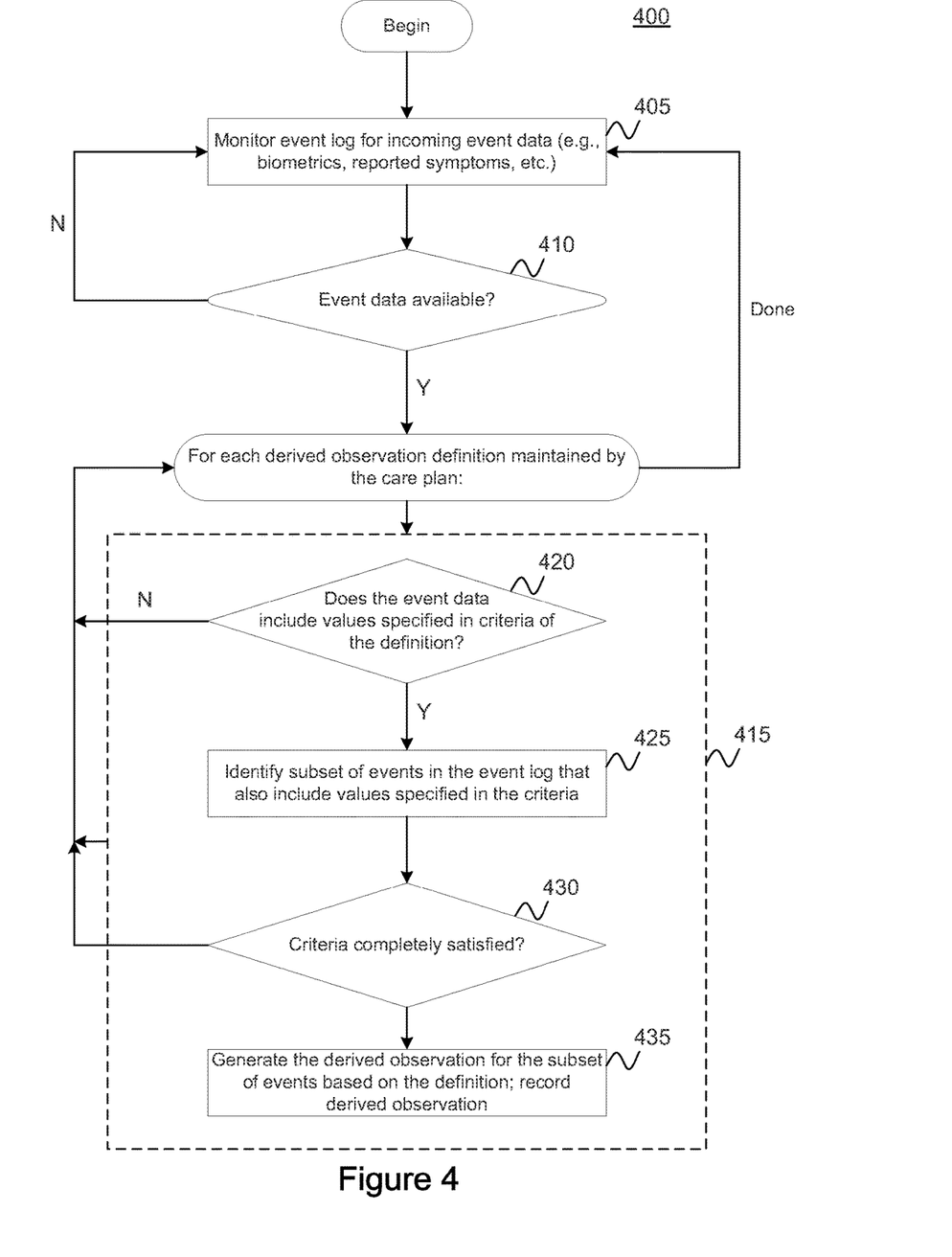
FIG. 4 illustrates a method for generating a derived observation for a care plan, according to one embodiment.

FIG. 4 illustrates a method for generating a derived observation for a care plan, according to one embodiment. Method 400 begins at step 405, where the monitoring component 210 monitors the event log incoming event data such as biometrics and reported symptoms. The monitoring component 210 determines whether any event data is available (at step 410). If not, then the monitoring component 305 continues to monitor the event log.

If so, the evaluation component 215 determines whether the event data stored in the event log satisfies any of the derived observation definitions maintained by the care plan (at step 415). To do so, the evaluation component 215 analyzes a temporal slice of the event log and identifies a subset of events based on the definition. Specifically, at step 420, the evaluation component 215 determines whether the event data includes values specified in criteria of the definition. For example, assume that a derived observation definition for weight change over a weeklong period includes criteria requiring weight metrics to be taken from between Monday 12:00 AM to Sunday 11:59 PM of a given week. Event data that includes weight metrics include values that are specified in the criteria. If the values are specified the criteria, then at step 425, the evaluation component 215 identifies the subset of events in a temporal slice of the event log that also include values specified in the criteria. Continuing the previous example, the evaluation component 215 may identify weight metrics captured between Monday 12:00 AM to Sunday 11:59 PM.

At step 430, the evaluation component 215 determines whether, given the most recent data collected, the criteria of the definition is completely satisfied. If so, then at step 435, the evaluation component 215 generates the derived observed for the subset of events based on the definition. Once generated, the evaluation component 215 records the derived observation in the care plan. The care plan management application 111 treats the derived observation as a metric that can be used to further analyze a patient's condition. Continuing the previous example, if the derived observation for weight gain over a weeklong period indicates that the patient has gained a significant amount of weight at a rapid rate, the care plan management application 111 may notify the care provider 101 in response. In turn, the care provider 101 can analyze the patient's observed metrics (e.g., daily caloric intake) and other information (e.g., medical prescription information) to determine a cause for such a rapid weight gain. Once generated, the derived observation can be used to create other derived observations, as illustrated by the method starting again at step 405.

Figure 5:
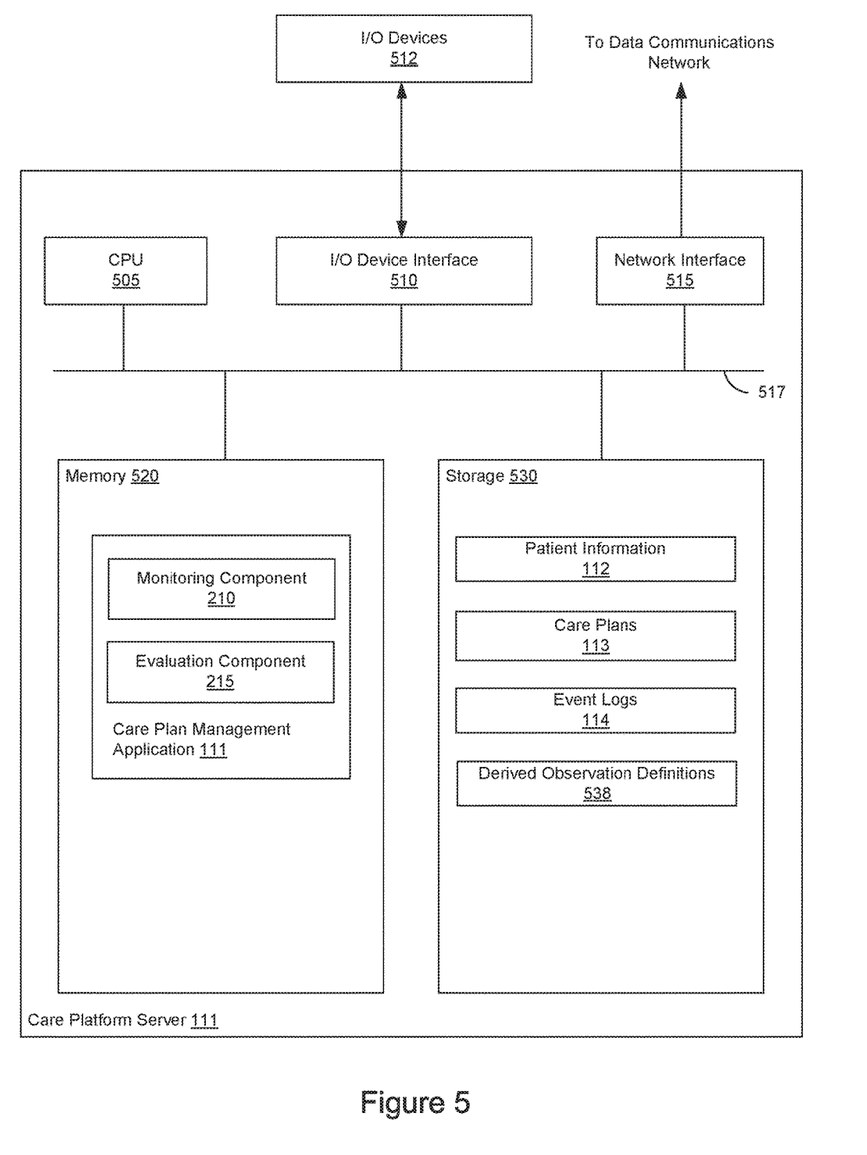
FIG. 5 illustrates an example care platform server configured to generate derived observations for a care plan, according to one embodiment.

FIG. 5 illustrates a care platform server 500 configured to generate derived observations for a care plan assigned to a patient, according to one embodiment. As shown, the care platform server 500 includes, without limitation, a central processing unit (CPU) 505, a network interface 515, a memory 520, and storage 530, each connected to a bus 517. The care platform server may also include an I/O device interface 510 connecting I/O devices 512 (e.g., keyboard, display and mouse devices) to the care platform server 500. Further, in context of this disclosure, the computing elements shown in the care platform server 500 may correspond to a physical computing system (e.g., a system in a data center) or may be a virtual computing instance executing within a computing cloud.

CPU 505 retrieves and executes programming instructions stored in memory 520 as well as stores and retrieves application data residing in the storage 530. The bus 517 is used to transmit programming instructions and application data between CPU 505, I/O devices interface 510, storage 530, network interface 515, and memory 520. Note, CPU 505 is included to be representative of a single CPU, multiple CPUs, a single CPU having multiple processing cores, and the like. Memory 520 is generally included to be representative of a random access memory. Storage 530 may be a disk drive storage device. Although shown as a single unit, storage 530 may be a combination of fixed and/or removable storage devices, such as fixed disc drives, removable memory cards, or optical storage, network attached storage (NAS), or a storage area-network (SAN).

Illustratively, memory 520 includes a care plan management application 522. And storage 530 includes patient information 532, care plans 534, event logs 536, and derived observation definitions 538. The care plan management application 522 further includes a monitoring component 524 and an evaluation component 526. The monitoring component 524 receives raw biometrics sent by a patient (e.g., via an application on the patient's mobile device) and stores the data in the events log 536 associated with the care plan 534 assigned to the patient. The sensor data can be obtained from various sensor devices (e.g., an adhesive body monitor, heart rate monitor, weight scale, blood pressure cuff, etc.) and may include a variety of patient biometrics, such as blood pressure, heart rate, weight, breath rate, calories burned per hour, whether the patient is active or sedentary, etc.

A care plan 534 is a set of tasks, thresholds, and other metrics targeted towards treating a certain condition (or group of conditions) diagnosed in a patient. Further, the care plan 534 includes derived observations, which are generated based on raw biometrics (e.g., heart rate, blood pressure, weight, etc.) obtained from the patient.

In one embodiment, the monitoring component 210 receives sensor data (i.e., biometric data) from the sensor devices of a patient and stores the data in the event log 536 corresponding to the care plan 534 of the patient. The evaluation component 526 determines whether data in the event log 536 satisfies criteria specified in one or more of the derived observation definitions 538. If so, then the evaluation component 526 generates a derived observation corresponding to the definition(s) 538 having the satisfied criteria.

One embodiment of the present disclosure is implemented as a program product for use with a computer system. The program(s) of the program product defines functions of the embodiments (including the methods described herein) and can be contained on a variety of computer-readable storage media. Examples of computer-readable storage media include (i) non-writable storage media (e.g., read-only memory devices within a computer such as CD-ROM or DVD-ROM disks readable by an optical media drive) on which information is permanently stored; (ii) writable storage media (e.g., floppy disks within a diskette drive or hard-disk drive) on which alterable information is stored. Such computer-readable storage media, when carrying computer-readable instructions that direct the functions of the present disclosure, are embodiments of the present disclosure. Other examples media include communications media through which information is conveyed to a computer, such as through a computer or telephone network, including wireless communications networks.

In general, the routines executed to implement the embodiments of the present disclosure may be part of an operating system or a specific application, component, program, module, object, or sequence of instructions. The computer program of the present disclosure is comprised typically of a multitude of instructions that will be translated by the native computer into a machine-readable format and hence executable instructions. Also, programs are comprised of variables and data structures that either reside locally to the program or are found in memory or on storage devices. In addition, various programs described herein may be identified based upon the application for which they are implemented in a specific embodiment of the disclosure. However, it should be appreciated that any particular program nomenclature that follows is used merely for convenience, and thus the present disclosure should not be limited to use solely in any specific application identified and/or implied by such nomenclature.

As described, embodiments herein provide techniques for automatically generating derived observations for a care plan assigned to a patient. A care platform generates the derived observations based on raw biometric data observed from the patient, e.g., blood pressure, weight, heart rate, PVCs, etc. The care platform evaluates the raw data against derived observation definitions to determine if the data may be used to generate a derived observation. If so determined, the care platform generates the derived observation. Advantageously, the care platform may use the generated derived observation in a variety of ways, such as by generating subsequent derived observations based on the previously generated ones, by alerting a care provider in the event that a derived observation exceeds a given threshold, etc.

While the foregoing is directed to embodiments of the present disclosure, other and further embodiments of the disclosure may be devised without departing from the basic scope thereof, and the scope thereof is determined by the claims that follow.

What is claimed is:

1. A method for generating a derived observation for a care plan assigned to a patient, the method comprising:
   identifying a care plan assigned to a patient, the care plan comprising a plurality of care protocols, each care protocol related to a medical condition of the patient;
   receiving, at a care plan management system from a remote device, data comprising a plurality of detected events relating to biometric data for the patient, wherein a first event of the plurality of detected events is initially classified as a first type of event using the remote device, and wherein the remote device has fewer computational resources relative to the care plan management system;
   selecting the first event, from among the plurality of detected events, for reclassification, based on the initial classification, and in response automatically reclassifying the first event as a second type of event using the care plan management system, wherein the second type of event is a sub-classification of the first type of event;
   identifying an event log comprising the plurality of detected events, including the reclassified first event, for the patient, wherein the care plan includes one or more definitions for metrics that are derived from at least some of the plurality of detected events;
   analyzing the one or more definitions included in the care plan to determine a time period;
   selecting a temporal slice of the event log based on the determined time period;
   generating the derived metrics by evaluating one or more events, of the plurality of detected events, within the selected temporal slice of the event log against one or more of the definitions;
   evaluating a condition of the patient based on the derived metrics; and
   determining that the derived metrics are over a predetermined threshold, and in response initiating a treatment process for the patient by modifying the care plan assigned to the patient.

2. The method of claim 1, further comprising:
   analyzing the care plan to determine the one or more definitions, wherein the one or more definitions specify bounds of the temporal slice to be taken from the event log; and
   determining, based on one or more of the definitions, that the events within the selected temporal slice of the event log may be used in one or more of the definitions.

3. The method of claim 1, wherein each derived metric is associated with a corresponding threshold, and the method further comprising upon determining that the derived metric exceeds the threshold, performing an action based on a rule associated with the threshold.

4. The method of claim 3, wherein performing the action comprises notifying a care provider of the patient of the exceeded threshold.

5. The method of claim 1, wherein the biometric data includes at least one of a blood pressure measure, a weight measure, a heart rate measure, a premature ventricular contraction, or a QT interval measure of a patient.

6. The method of claim 1, wherein the temporal slice includes a subset of the plurality of events observed within a specified time range from a first point within the event log.

7. The method of claim 1, wherein generating the derived metrics is further based on a difference between a biometric data value from an event within the temporal slice of the event log and a previous biometric data value collected for the patient.

8. The method of claim 1, wherein generating the derived metrics is based on data values relating to a first type of biometric data, data values relating to a second type of biometric data, and a second derived metric generated according to a second definition specified within the care plan by evaluating events within the event log against the second definition.

9. The method of claim 1, further comprising:
generating a second derived metric by evaluating events within the selected temporal slice of the event log against a second one or more of the definitions, wherein the second derived metric is generated by construing data values for a first type of biometric data relative to other data values for the first type of biometric data over a window of time defined by the temporal slice.

10. The method of claim 1, wherein reclassifying the first event as the second type of event using the care plan management system uses more computing resources than initially classifying the first event as the first type of event using the remote device.

11. The method of claim 10, wherein initially classifying the first event as the first type of event using the remote device, and reclassifying the first event as the second type of event using the care plan management system, allows for analysis of the data to be performed using computing resources of the care provider environment, rather than the relatively fewer resources of the remote device, while determining the initial classification for the event using the remote device.

12. The method of claim 10, wherein the remote device is a monitoring device configured to collect biometric data from the patient.

13. The method of claim 1, wherein reclassifying the first event as a second type of event using the care plan management system further comprises:
determining, based on the initial classification, a plurality of sub-classifications associated with the initial classification; and
selecting a first sub-classification, of the plurality of sub-classifications, as the second type of event, based on received biometric data related to the first event.

14. A non-transitory computer-readable storage medium storing instructions, which, when executed on a processor, performs an operation for generating a derived observation for a care plan assigned to a patient, the operation comprising:
identifying a care plan assigned to a patient, the care plan comprising a plurality of care protocols, each care protocol related to a medical condition of the patient;
receiving, at a care plan management system from a remote device, data comprising a plurality of detected events relating to biometric data for the patient, wherein a first event of the plurality of detected events is initially classified as a first type of event using the remote device, and wherein the remote device has fewer computational resources relative to the care plan management system;
selecting the first event, from among the plurality of detected events, for reclassification, based on the initial classification, and in response automatically reclassifying the first event as a second type of event using the care plan management system, wherein the second type of event is a sub-classification of the first type of event;
identifying an event log comprising the plurality of detected events, including the reclassified first event, for the patient, wherein the care plan includes one or more definitions for metrics that are derived from at least some of the plurality of detected events;
analyzing the one or more definitions included in the care plan to determine a time period;
selecting a temporal slice of the event log based on the determined time period;
generating the derived metrics by evaluating one or more events, of the plurality of detected events, within the selected temporal slice of the event log against one or more of the definitions;
evaluating a condition of the patient based on the derived metrics; and
determining that the derived metrics are over a predetermined threshold, and in response initiating a treatment process for the patient by modifying the care plan assigned to the patient.

15. The computer-readable storage medium of claim 14, wherein generating the derived metrics is further based on a difference between a biometric data value from an event within the temporal slice of the event log and a previous biometric data value collected for the patient.

16. The computer-readable storage medium of claim 14, wherein generating the derived metrics is based on data values relating to a first type of biometric data, data values relating to a second type of biometric data, and a second derived metric generated according to a second definition specified within the care plan by evaluating events within the event log against the second definition.

17. A system, comprising:
a processor; and
a memory storing one or more application programs configured to perform an operation for generating a derived observation for a care plan assigned to a patient, the operation comprising:
identifying a care plan assigned to a patient, the care plan comprising a plurality of care protocols, each care protocol related to a medical condition of the patient;
receiving, at a care plan management system from a remote device, data comprising a plurality of detected events relating to biometric data for the patient, wherein a first event of the plurality of detected events is initially classified as a first type of event using the remote device, and wherein the remote device has fewer computational resources relative to the care plan management system;
selecting the first event, from among the plurality of detected events, for reclassification, based on the initial classification, and in response automatically reclassifying the first event as a second type of event using the care plan management system, wherein the second type of event is a sub-classification of the first type of event;
identifying an event log comprising the plurality of detected events, including the reclassified first event, for the patient, wherein the care plan includes one or more definitions for metrics that are derived from at least some of the plurality of detected events;
analyzing the one or more definitions included in the care plan to determine a time period;

selecting a temporal slice of the event log based on the determined time period;

generating the derived metrics by evaluating one or more events, of the plurality of detected events, within the selected temporal slice of the event log against one or more of the definitions;

evaluating a condition of the patient based on the derived metrics; and determining that the derived metrics are over a predetermined threshold, and in response initiating a treatment process for the patient by modifying the care plan assigned to the patient.

18. The system of claim 17, wherein generating the derived metrics is further based on a difference between a biometric data value from an event within the temporal slice of the event log and a previous biometric data value collected for the patient.

19. The system of claim 17, wherein generating the derived metrics is based on data values relating to a first type of biometric data, data values relating to a second type of biometric data, and a second derived metric generated according to a second definition specified within the care plan by evaluating events within the event log against the second definition.

20. The method of claim 10, wherein the first type of event is a cardiac event, wherein selecting the first event, from among the plurality of detected events, for reclassification is based on the initial classification of the first type of event as a cardiac event, and wherein the second type of event is a sub-classification of the cardiac event.

* * * * *